United States Patent [19]

Valus et al.

[11] Patent Number: 4,661,629

[45] Date of Patent: Apr. 28, 1987

[54] SEPARATION OF PHENYLALANINE FROM PHENYLALANINE ETHYL ESTER

[75] Inventors: Ronald J. Valus, Valley View; James C. Davis, Hudson, both of Ohio

[73] Assignee: The Standard Oil Company, Cleveland, Ohio

[21] Appl. No.: 803,754

[22] Filed: Dec. 2, 1985

[51] Int. Cl.$^4$ ............................................. C07C 99/12
[52] U.S. Cl. ...................................... 562/443; 560/38
[58] Field of Search .................. 562/443, 445; 560/38; 425/276

[56] References Cited

U.S. PATENT DOCUMENTS 3,257,334   6/1966   Chen et al. .......................... 525/276
4,464,498   8/1984   Sugiura ............................... 562/445
4,584,399   4/1986   Portal et al. ........................ 562/443
4,584,400   4/1986   Otani et al. ......................... 562/443

OTHER PUBLICATIONS

Tozawa et al., Chem. Abst., vol. 93, #26742p (1980).
Lippold et al., Chem. Abst., vol. 101, #43446w (1984).

Primary Examiner—James H. Reamer
Attorney, Agent, or Firm—Charles S. Lynch; John E. Miller; Larry W. Evans

[57] ABSTRACT

Separating phenylalanine from its admixture with phenylalanine ethyl ester by preferential permeation through a sulfonated polystyrene cation exchange resin membrane.

1 Claim, No Drawings

SEPARATION OF PHENYLALANINE FROM PHENYLALANINE ETHYL ESTER

This invention relates to separating phenylalanine ethyl ester by preferential permeation through a sulfonated polystyrene cation exchange resin membrane.

Phenylalanine can be made synthetically as is well known in the art. An example is the Strecher synthesis, starting with benzaldehyde, $NH_3$ and HCN. See "Synthetic Production and Utilization of Amino Acids" by T. Kaneko, John Wiley and Sons, N.Y. 1974. See also Japanese patent publication No. 75-05702 Mar. 6, 1975, filed as application No. 70-71,745 on Aug. 18, 1970 (C.A. 76:79612W). Of course, such methods produce a mixture of L- and D-phenylalanine. When it is desired to obtain the L or the D form substantially free of its enantiomer, the mixture can be esterified to the ethyl ester, for instance. Then it can be treated with an esterase effective to selectively hydrolyze only one of the isomers. For instance, a carboxyl esterase, α-chymotrypsin or other proteases than have esterase activity can be used to catalyze the hydrolysis of only the L-phenylalanine ethyl ester to obtain a mixture containing L-phenylalanine and both L- and D-phenylalanine ethyl esters, or a mixture containing only L-phenylalanine and D-phenylalanine ethyl ester, depending on the degree of the hydrolysis. An example of the utility of the present invention is separation of the phenylalanine from such a mixture to form a product greatly enriched in such phenylalanine in comparison to the starting material mixture.

In accordance with the present invention there is provided a method of separating phenylalanine from its mixture with phenylalanine ethyl ester by contacting one side of a membrane with a solution of said mixture and allowing said phenylalanine to preferentially permeate to the other side of said membrane, and collecting said permeated phenylalanine greatly enriched with respect of said phenylalanine ethyl ester, said membrane comprising a permeable sulfonated polystyrene cationic exchange resin.

In an illustrative specific example a mixture of 50 mole percent of L-phenylalanine and 50 mole percent of D,L-phenylalanine ethyl ester hydrochloride is provided.

This mixture was separated by a cation exchange membrane, Raipore 1010, a product of RAI Research Corporation, Hauppauge, L.I. N.Y. It is a sulfonated polystyrene graft of a one mil thick polytetrafluoroethylene preformed film. It was made by contacting the surface of the PTFE film with styrene monomer and exposing to high energy radiation. The radiation polymerized the styrene and grafted the polymer to the PTFE. Thereafter, the polystyrene was sulfonated. It had the following nominal properties:

RESISTANCE (ohm-cm$^2$) 0.6N KCl: 0.2–0.5
SELECTIVITY (0.5N KCl/1.0N KCL) (%): 86
ION EXCHANGE CAPACITY (meq/g): 1.2
GEL WATER (% DRY BASIS): 20
THICKNESS (WET IN MILS): 2

The membrane was stored in methanol until used. Before use, the membrane was treated with 1N sulfuric acid for approximately 30 minutes. It was then rinsed with distilled water, and thereafter with a mixture of 50 volumes of ethanol and 50 volumes of water. The film was placed in a CECI eluate concentrator from Amicon Corporation. The top half of the cell forms a spiral chamber fitting over the membrane. The membrane is placed on top of a porous plastic support disk and brought into contact with the down facing, open side of the spiral chamber. The membrane thus formed the bottom wall of the spiral chamber. The spiral chamber had a feed inlet near the center of the spiral and a fluid outlet at the periphery of the spiral chamber. The diameter of the circular membrane was 90 mm., and the effective area thereof was 43 sq. cm. A thin chamber closed the bottom side of the cell in such a manner that fluid passing through the membrane was collected in the lower chamber. This lower chamber also had a fluid inlet and a fluid outlet.

The 50/50 mixture of L-phenylalanine and D,L-phenylalanine ethyl ester hydrochloride was dissolved in a mixture of 50 volumes of water and 50 volumes of absolute ethanol to form 210 ml of a solution having a 0.01 molar concentration of each component. Of course, on solution the D,L-phenylalanine ethyl ester hydrochloride became D,L-phenylalanine ethyl ester. This test solution was stored in a chamber and was continuously pumped through the spiral top chamber. At the same time 70 ml of a solution of 50 volumes of absolute ethanol and 50 volumes of water were stored in another receptacle, and this was continuously circulated through the lower chamber and back to the receptacle. As the process proceeded, the part of the feed that passed through the membrane accumulated in the lower chamber. The test was run at room temperature. After 6 hours of operation the ratio of phenylalanine to phenylalanine ethyl ester in the sweep solution was 24.28, or 4 moles of phenylalanine ethyl ester for each 96 moles of phenylalanine, as determined by analysis using high pressure liquid chromatography.

As will be evident to those skilled in the art various modifications of this invention can be made or followed in the light of the foregoing disclosure and discussion without departing from the spirit and scope of the disclosure or from the scope of the claims.

We claim:

1. A method of separating phenylalanine from its mixture with phenylalanine ethyl ester by contacting one side of a membrane with a solution of said mixture and allowing said phenylalanine to preferentially permeate to the other side of said membrane, and collecting said permeated phenylalanine greatly enriched with respect to said phenylalanine ethyl ester, said membrane being a permeable sulfonated polystyrene cationic exchange resin on polytetrafluoroethylene.

* * * * *